United States Patent
Tsukada et al.

(10) Patent No.: US 9,494,547 B2
(45) Date of Patent: Nov. 15, 2016

(54) GAS SENSOR CONTROL APPARATUS AND METHOD

(75) Inventors: Hiroyuki Tsukada, Iwakura (JP); Norikazu Ieda, Ichinomiya (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 576 days.

(21) Appl. No.: 13/175,711

(22) Filed: Jul. 1, 2011

(65) Prior Publication Data

US 2012/0001641 A1    Jan. 5, 2012

(30) Foreign Application Priority Data

Jan. 7, 2009    (JP) .................................. 2009-001410

(51) Int. Cl.
*G01N 27/407* (2006.01)
*G01N 27/406* (2006.01)

(52) U.S. Cl.
CPC ........ *G01N 27/407* (2013.01); *G01N 27/4065* (2013.01)

(58) Field of Classification Search
USPC .............. 204/406, 424–429; 205/783.5–785
See application file for complete search history.

(56) References Cited

U.S. PATENT DOCUMENTS

| | | | |
|---|---|---|---|
| 6,384,386 B2 * | 5/2002 | Hashimoto | G01N 27/122 123/697 |
| 7,142,976 B2 | 11/2006 | Inoue et al. | |
| 2006/0157348 A1 * | 7/2006 | Inoue et al. | 204/401 |
| 2006/0219553 A1 * | 10/2006 | Ieda et al. | 204/424 |
| 2008/0060941 A1 | 3/2008 | Ieda et al. | |

FOREIGN PATENT DOCUMENTS

JP       3833687 B2    7/2006
JP    2008-70194 A    3/2008

* cited by examiner

*Primary Examiner* — Luan Van
*Assistant Examiner* — Steven Rosenwald
(74) *Attorney, Agent, or Firm* — Sughrue Mion, PLLC

(57) ABSTRACT

A gas sensor control apparatus (1) includes a gas sensor (8) having an oxygen pump cell (14); a sensor drive circuit (52) which energizes the gas sensor; terminal voltage output means (54) which detects and outputs a terminal voltage of the oxygen pump cell; anomaly detection means (58) which compares the terminal voltage and a first threshold value, and when the terminal voltage exceeds the first threshold value, outputs a short circuit anomaly signal informing of a short circuit; a controller (55) which compares the terminal voltage and a second threshold value less than the first threshold value, and when the terminal voltage exceeds the second threshold value, generates a cell voltage anomaly signal informing of an application of an overvoltage to the oxygen pump cell; and command means (9) which, when receiving the short circuit anomaly signal or cell voltage anomaly signal, outputs a de-energization command.

4 Claims, 6 Drawing Sheets

FIG.4

| ENERGIZATION STATE (OPERATION MODE) | SWITCH | | | | |
|---|---|---|---|---|---|
| | SW1 | SW2 | SW3 | SW4 | SW5 |
| GAS CONCENTRATION MEASURING ENERGIZATION STATE | OFF | ON | ON | OFF | ON |
| SENSOR PROTECTION ENERGIZATION STATE | OFF | OFF | OFF | OFF | OFF |
| PRE-ACTIVATION ENERGIZATION STATE | ON | OFF | OFF | ON | ON |

GAS SENSOR CONTROL APPARATUS AND METHOD

TECHNICAL FIELD

The invention relates to a sensor control apparatus and method which control a gas sensor having at least an oxygen pump cell including a solid electrolyte body and a pair of electrodes provided on the solid electrolyte body.

BACKGROUND ART

An oxygen sensor which detects an oxygen concentration in an exhaust gas and an air-fuel ratio sensor are known as a gas sensor which carries out a fuel efficiency improvement and combustion control of an internal combustion engine of an automobile or the like. Also, a reduction in the amount of nitrogen oxide ($NO_X$) in the exhaust gas is required in keeping with a tightening of automobile exhaust gas regulations, and an $NO_X$ sensor which can directly measure an $NO_X$ concentration is being developed.

Each of these gas sensors has a gas sensor element including one or a plurality of cells, each of which has a pair of electrodes formed on the surface of an oxygen ion conducting solid electrolyte such as zirconia, and carries out a specified gas concentration detection based on an output from the gas sensor element.

Also, each of these gas sensors incorporates a heater for activating the solid electrolyte.

As these gas sensors, there is known a linear air-fuel ratio sensor (hereafter referred to also as a UEGO sensor) which, having two cells (an oxygen concentration sensing cell and an oxygen pump cell) disposed in such a way as to sandwich a measuring chamber, introduces a measured gas into the measuring chamber via a diffusion resistor, and detects oxygen contained in the measured gas. Furthermore, an $NO_X$ gas sensor in which a cell which detects an $NO_X$ gas concentration is disposed in addition to the two cells (the oxygen concentration sensing cell and the oxygen pump cell), and which has a total of three cells, is also known.

A sensor drive circuit is connected to this kind of gas sensor, and the gas sensor energizes the cells via the sensor drive circuit, measures a specified gas concentration in the measured gas based on outputs from the cells, and is called a gas sensor control apparatus, including the sensor drive circuit. Also, as an energization state in which the cells are energized, there are a protection energization state for protecting the gas sensor, a pre-activation energization state in which the gas sensor in a deactivated condition is energized with a minute current, a gas concentration measuring energization state for detecting a specified gas, and the like.

Among them, the protection energization state is such that, by electrically cutting off the continuity between the cells and sensor drive circuit, a current is prevented from flowing through the gas sensor, thus protecting the gas sensor. Also, the pre-activation energization state is a mode in which oxygen which is of a reference concentration is accumulated in a reference oxygen chamber of, for example, the oxygen concentration sensing cell by the cell being energized with a minute current, thus preparing for a gas concentration measurement.

However, it may happen that an anomaly, such as a short circuit with a battery or the ground, or a disconnection, occurs in a wire of the sensor drive circuit or gas sensor. Then, when the gas concentration measuring energization state in which a gas concentration is measured continues despite the fact that such a wire anomaly occurs, there is fear that an excessively high current flows through the gas sensor, and that the gas sensor is damaged.

For this kind of reason, a technology is being developed whereby, when a wire anomaly is detected, the connection of the sensor drive circuit side and gas sensor is electrically cut off, creating the protection energization state, and subsequently, anomaly contents and a site of occurrence of the anomaly are diagnosed (refer to Patent Document 1). Because of this, no more anomalous current continues to flow through the gas sensor, thus preventing the gas sensor being damaged.

Also, when a command to switch from another energization state to the gas concentration measuring energization state is output to the sensor drive circuit without recognizing a wire anomaly, there is fear that an excessively high current flows through the gas sensor, and that the gas sensor is damaged, in the same way.

For this kind of reason, a technology is being developed whereby a switching to the gas concentration measuring energization state is allowed only when the preceding state is the pre-activation energization state, thereby detecting an anomaly without damaging the gas sensor (refer to Patent Document 2). Because of this, in the event of the pre-activation energization state in which a minute current is caused to flow through the gas sensor even when a wire anomaly occurs, a voltage applied to the gas sensor departs from a normal range, meaning that it is possible to detect the wire anomaly.

Also, in the case of the heretofore known gas sensor control apparatus, a constant voltage source which applies a target voltage for controlling an Ip current flowing through the oxygen pump cell is provided in the sensor drive circuit, and the target voltage is supplied to a PID control circuit in the sensor drive circuit. Then, a configuration is such that an amount of deviation between an actual output voltage of the oxygen concentration sensing cell and the target voltage is PID computed by the PID control circuit in accordance with the oxygen concentration in the measuring chamber, and an Ip current in accordance with the amount of deviation flows through the oxygen pump cell.

Then, there is provided a Vp limiter which, when a terminal voltage of the oxygen pump cell exceeds a threshold value at which it becomes an overvoltage causing a blackening, changes the target voltage, and prevents the overvoltage from being applied.

RELATED ART DOCUMENTS

Patent Documents

[Patent Document 1] Japanese Patent No. 3,833,687
[Patent Document 2] JP-A-2008-70194

DISCLOSURE OF THE INVENTION

Problems that the Invention is to Solve

However, when the heretofore described Vp limiter is provided, there is a case in which the sensor drive circuit becomes larger, and the number of parts increases, leading to an increase in cost.

That is, the invention has an object of providing a gas sensor control apparatus and method with which it is possible to prevent an application of an overvoltage to an oxygen pump cell.

Means for Solving the Problems

In order to solve the heretofore problem, the gas sensor control apparatus of the invention includes a gas sensor having at least an oxygen pump cell including a solid electrolyte body and a pair of electrodes provided on the solid electrolyte body; a sensor drive circuit which, being connected to the gas sensor, energizes the gas sensor in order to drive the gas sensor; terminal voltage output means which detects and outputs a terminal voltage of the oxygen pump cell; anomaly detection means which compares the terminal voltage and a first threshold value, and when the terminal voltage exceeds the first threshold value, outputs a short circuit anomaly signal informing of a short circuit between a supply voltage which drives the gas sensor and the electrodes; a controller which compares the terminal voltage and a second threshold value less than the first threshold value, and when the terminal voltage exceeds the second threshold value, generates a cell voltage anomaly signal informing of an application of an overvoltage to the oxygen pump cell; and command means which, when receiving the short circuit anomaly signal or cell voltage anomaly signal, outputs a de-energization command for setting the sensor drive circuit to be de-energized.

By adopting this kind of configuration, it is possible to effectively prevent the application of an overvoltage to the oxygen pump cell.

The command means may be configured in such a way that it outputs the de-energization command after the elapse of a first predetermined time from receiving the short circuit anomaly signal, while it outputs the de-energization command after the elapse of a second predetermined time longer than the first predetermined time from receiving the cell voltage anomaly signal.

Normally, when causing the gas sensor to make a transition from the pre-activation energization state to the gas concentration measuring energization state, an Ip current is caused to flow in a condition in which the resistance of the oxygen pump cell is high, so the voltage of the oxygen pump cell increases above the overvoltage, but in the event that the gas sensor is normal, the voltage of the oxygen pump cell drops to less than the overvoltage in the order of several seconds. Therefore, when the cell voltage anomaly signal is generated even when the second predetermined time is exceeded, it is determined that the voltage of the oxygen pump cell is anomalous, and it is thereby possible to prevent an anomaly from being falsely detected.

Furthermore, when receiving the short circuit anomaly signal informing that there is a possibility that the cell is short-circuited, it is necessary to output the de-energization command immediately (after the elapse of the first predetermined time), but when receiving the cell voltage anomaly signal with less urgency, it is sufficient to output the de-energization command when the second predetermined time later than the first predetermined time elapses.

The gas sensor control method of the invention, being a control method of a gas sensor control apparatus including a gas sensor having at least an oxygen pump cell including a solid electrolyte body and a pair of electrodes provided on the solid electrolyte body, and a sensor drive circuit which, being connected to the gas sensor, energizes the gas sensor in order to drive the gas sensor, includes a terminal voltage output step which detects and outputs a terminal voltage of the oxygen pump cell; an anomaly detection step which compares the terminal voltage and a first threshold value, and when the terminal voltage exceeds the first threshold value, outputs a short circuit anomaly signal informing of a short circuit between a supply voltage which drives the gas sensor and the electrodes; a cell voltage anomaly signal generation step which compares the terminal voltage and a second threshold value less than the first threshold value, and when the terminal voltage exceeds the second threshold value, generates a cell voltage anomaly signal informing of an application of an overvoltage to the oxygen pump cell; and a de-energization setting step which, when receiving the short circuit anomaly signal or cell voltage anomaly signal, sets the sensor drive circuit to be de-energized.

In the de-energization setting step, the sensor drive circuit may be set to be de-energized after the elapse of a first predetermined time from receiving the short circuit anomaly signal, while the sensor drive circuit may be set to be de-energized after the elapse of a second predetermined time longer than the first predetermined time from receiving the cell voltage anomaly signal.

Advantage of the Invention

According to the invention, it is possible to effectively prevent the application of the overvoltage to the oxygen pump cell.

BRIEF DESCRIPTION OF THE DRAWINGS

FIG. 4 is an illustration representing a condition of each switch for each energization state (operation mode).

MODE FOR CARRYING OUT THE INVENTION

Hereafter, a description will be given of an embodiment of the invention.

Figure 1:
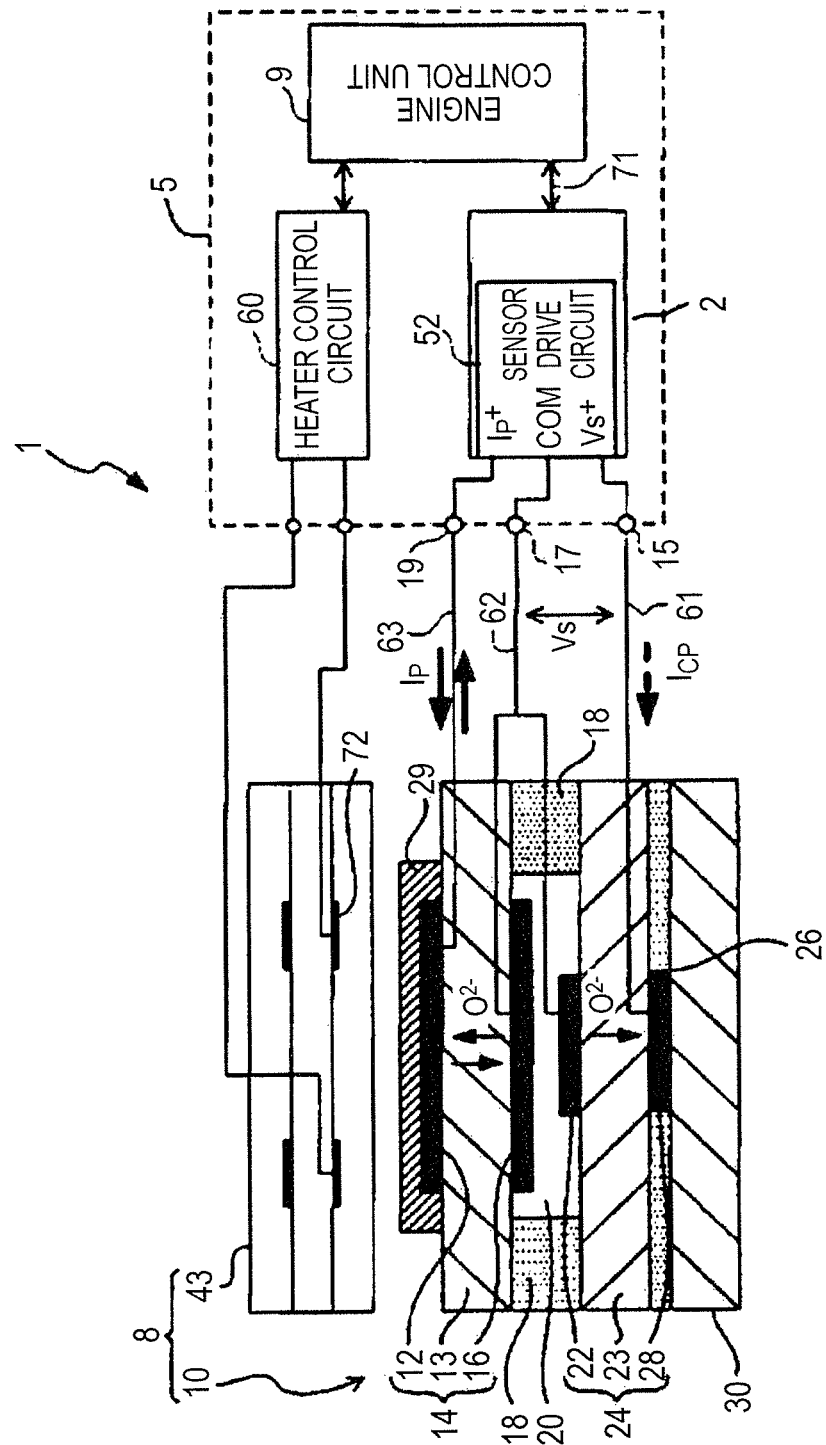
FIG. 1 is an outline configuration diagram of an internal combustion engine control system including an electronic control unit.

FIG. 1 is a schematic diagram showing a configuration of a gas sensor control apparatus 1 (an internal combustion engine control system) according to the embodiment of the invention including an electronic control unit (ECU) 5. The gas sensor control apparatus 1 executes various kinds of control process for controlling the operating condition of an internal combustion engine (an engine), and executes a process of detecting the concentration of a specified gas (oxygen or the like) contained in a measured gas (an exhaust gas).

The gas sensor control apparatus 1 includes the electronic control unit 5 and a gas sensor 8, and the gas sensor 8 is mounted in an exhaust pipe of the engine. The electronic control unit 5 includes a sensor control circuit 2 which controls the gas sensor 8 (a sensor element 10), an engine control unit 9 (hereafter referred to also as an "engine CPU" 9), and a heater control circuit 60 which controls a heater 43, and the sensor control circuit 2 includes a sensor drive circuit 52. The engine control unit 9, being connected to the heater control circuit 60, controls the heater control circuit 60 in such a way that the temperature of the sensor element 10 reaches an operating temperature (hereafter referred to also as an activation temperature, for example, 550 to 900° C.). Also, the engine control unit 9, being connected to the sensor control circuit 2 via a transmission cable 71, controls the sensor control circuit 2.

The gas sensor 8, including the sensor element 10 which detects the oxygen concentration in the measured gas (exhaust gas) over a wide area and the heater 43 for maintaining the sensor element 10 at the operating temperature, acts as a so-called linear air-fuel ratio sensor. Also, the sensor element 10 includes an oxygen pump cell 14, a porous diffusion layer 18, an oxygen concentration sensing cell 24, and a reinforcing plate 30. A detailed configuration of the gas sensor 8 will be described hereafter.

The sensor control circuit 2 includes the sensor drive circuit 52 electrically connected to the gas sensor 8, and the like. The sensor drive circuit 52, by energizing the gas sensor 8 (the oxygen pump cell 14 and oxygen concentration sensing cell 24), carries out a drive control thereof, and detects an output (a gas detection signal) from the oxygen pump cell 14 and an element resistance value signal. The sensor control circuit 2 outputs the detected gas detection signal and element resistance value signal to the engine control unit 9.

The sensor control circuit 2 can be realized as, for example, an ASIC (application specific integrated circuit). Also, the gas detection signal, varying in accordance with the oxygen concentration in the measured gas, is used to measure the oxygen concentration. Meanwhile, the element resistance value signal indicates the electrical resistance value of the gas sensor 8, and varies in accordance with the temperature of the gas sensor 8, but as a detection of the element resistance value signal and a calculation of the temperature of the gas sensor 8 can be carried out using a heretofore known technique, details are omitted.

The sensor control circuit 2 (sensor drive circuit 52) includes a Vs+ terminal, a COM terminal, and an $Ip_+$ terminal, and the individual terminals are electrically connected respectively to a first connection terminal 15, second connection terminal 17, and third connection terminal 19 of the electronic control unit 5. Then, a second sensing electrode 28 of the sensor element 10, to be described hereafter, is electrically connected to the Vs+ terminal of the sensor control circuit 2 via the first connection terminal 15 and a wire 61. Also, a first sensing electrode 22 and second pump electrode 16 of the sensor element 10 are electrically connected to the COM terminal of the sensor control circuit 2 via the second connection terminal 17 and a wire 62. In the same way, a first pump electrode 12 of the sensor element 10 is electrically connected to the Ip+ terminal of the sensor control circuit 2 via the third connection terminal 19 and a wire 63. By so doing, the sensor drive circuit 52 is electrically connected to the gas sensor 8, thus sensing the gas detection signal and element resistance value signal.

A controller 55 can be configured of a logic circuit which executes various kinds of control process in the sensor control circuit 2.

The engine control unit 9 can be configured of a microcomputer including a CPU acting as a central processing unit, memories (an RAM and ROM) storing data, programs, and the like, and an input port and output port which carry out an input and output of signals to and from an external instrument. The engine control unit 9, by the CPU executing various kinds of computation process based on the programs stored in the memories, controls an execution of a computation instruction, data transfer instruction, or the like. Also, the engine control unit 9 reflects a signal input into the input port in the contents of an input port register, and outputs contents stored in an output port register to the output port as a signal.

Then, the engine control unit 9, as well as determining an energization state (an energization direction, a current integrated value, and the like) in which an Ip current flows through the oxygen pump cell 14, to be described hereafter, based on a gas detection signal Vip output from the sensor control circuit 2, computes an oxygen concentration based on the Ip current energization state. The engine control unit 9, by executing the combustion control of the engine, or the like, using the oxygen concentration obtained from the computation, controls the operating condition of the internal combustion engine.

Furthermore, the engine control unit 9 also executes a command output process which outputs a command to switch the energization state (hereafter referred to as a "switching command" as appropriate), to be described hereafter, to the sensor control circuit 2, and an oxygen pump cell protection process which controls a terminal voltage of the oxygen pump cell 14 when a voltage causing an overvoltage is applied to the oxygen pump cell 14.

The engine control unit 9 corresponds to "command means" in the claims.

Next, a description will be given of a configuration of the gas sensor 8.

The oxygen pump cell 14 has an oxygen ion conducting solid electrolyte body 13 formed plate-like from partially stabilized zirconia ($ZrO_2$) and a first pump electrode 12 and second pump electrode 16 formed mainly from platinum on the front surface and rear surface respectively of the solid electrolyte body 13. The first pump electrode 12 is electrically connected to the third connection terminal 19 of the electronic control unit 5 via the wire 63, and the second pump electrode 16 is electrically connected to the second connection terminal 17 of the electronic control unit 5 via the wire 62. The first pump electrode 12, being covered with a porous protective layer 29, is protected from a toxic substance or the like by the porous protective layer 29.

The oxygen concentration sensing cell 24 has an oxygen ion conducting solid electrolyte body 23 formed plate-like from partially stabilized zirconia ($ZrO_2$) and the first sensing electrode 22 and second sensing electrode 28 formed mainly from platinum on the front surface and rear surface respectively of the solid electrolyte body 23. The first sensing electrode 22 is electrically connected to the second connection terminal 17 of the electronic control unit 5 via the wire 62, and electrically connected to the second pump electrode 16 too. The second sensing electrode 28 is electrically connected to the first connection terminal 15 of the electronic control unit 5 via the wire 61.

An insulating layer (not shown) which, being based on an insulating material (alumina or the like), electrically insulates the oxygen pump cell 14 and oxygen concentration sensing cell 24 from each other is interposed between the two cells 14 and 24, and the porous diffusion layer 18 is provided in one portion of the insulating layer. The porous diffusion layer 18 is formed to be porous based on an insulating material (alumina or the like) in order to carry out a diffusion control of the measured gas introduced into the interior of the sensor element 10. In place of the porous diffusion layer 18, pores may be disposed in a sidewall of the heretofore described insulating layer as a diffusion controlling portion.

A void measuring chamber 20 surrounded by the porous diffusion layer 18 and heretofore described insulating layer (not shown) is formed between the oxygen pump cell 14 and oxygen concentration sensing cell 24. The measuring chamber 20 is brought into communication with a measured gas atmosphere via the porous diffusion layer 18 (specifically, the porous portion). Also, the second pump electrode 16 is exposed on the upper surface of the measuring chamber 20, and the first sensing electrode 22 is exposed on the lower surface of the measuring chamber 20.

Also, the reinforcing plate 30 is stacked on a surface of the oxygen concentration sensing cell 24 on a side opposite to that of a surface thereof facing the measuring chamber 20, thus improving the overall strength of the sensor element 10. The reinforcing plate 30, having approximately the same size as each solid electrolyte body 13 and 23, is formed plate-like from a ceramic based material.

Then, the second sensing electrode 28 is cut off from the exterior by being sandwiched between the reinforcing plate 30 and oxygen ion conducting solid electrolyte body 23, and a reference oxygen chamber 26 acting as an enclosed space is formed around the second sensing electrode 28. Consequently, by energization with a minute constant current Icp in a direction from the second sensing electrode 28 toward the first sensing electrode 22, and by a pumping of oxygen from the measuring chamber 20 to the second sensing electrode 28 side, oxygen of an approximately constant concentration is accumulated in the reference oxygen chamber 26. By so doing, the oxygen in the reference oxygen chamber 26 reaches a reference oxygen concentration used when detecting the oxygen concentration.

Meanwhile, the flat plate-like heater 43 is disposed so as to be opposed to the oxygen pump cell 14 of the sensor element 10. The heater 43, being formed from an alumina based material, includes therein a heater wire 72 formed from a platinum based material. The heater 43 is controlled by power supplied from the heater control circuit 60, to be described hereafter, in such a way that the temperature of the sensor element 10 reaches the activation temperature (in the embodiment, 830° C.). Also, both ends of the heater wire 72 are electrically connected to the heater control circuit 60. Then, the sensor element 10 (the oxygen pump cell 14 and oxygen concentration sensing cell 24 thereof) is heated by the heater 43 and thereby activated, thus enabling a gas detection (an oxygen detection).

Next, a description will be given of an action of the gas sensor 8 (sensor element 10).

Firstly, the measured gas (exhaust gas) diffuses to the measuring chamber 20 via the porous diffusion layer 18. At this time, in a condition in which an air-fuel mixture (that is, the measured gas in the measuring chamber 20) supplied to the engine is maintained at a theoretical air-fuel ratio, an electromotive force of 450 [mV] occurs in the oxygen concentration sensing cell 24 (a potential difference of 450 [mV] occurs between the first sensing electrode 22 and second sensing electrode 28) due to an oxygen concentration difference between the measuring chamber 20 and the reference oxygen chamber 26 which is an oxygen concentration reference.

However, the concentration of oxygen contained in the exhaust gas changes, and the oxygen concentration in the measured gas contained in the measuring chamber 20 also changes, in accordance with a change in air-fuel ratio of the air-fuel mixture supplied to the engine. Therefore, with the internal combustion engine control system 1 of the embodiment, the Ip current flowing through the oxygen pump cell 14 is controlled by the sensor control circuit 2 in such a way that the potential difference between the first sensing electrode 22 and second sensing electrode 28 is maintained at 450 [mV]. That is, a pumping of oxygen is carried out by the oxygen pump cell 14 by the Ip current being controlled in such a way that the atmosphere of the measuring chamber 20 attains a condition the same as the theoretical air-fuel ratio.

Then, the oxygen pump cell 14 is configured so as to be able to switch between a pumping of oxygen from the measuring chamber 20 and a pumping of oxygen into the measuring chamber 20 in accordance with an energization direction of a current causing energization between a pair of electrodes (the first pump electrode 12 and second pump electrode 16). Also, the oxygen pump cell 14 is configured so as to be able to adjust the amount of oxygen pumped in accordance with the size of the Ip current causing energization between the pair of electrodes. Because of this, it is possible to compute the oxygen concentration in the measured gas based on the Ip current energization state (the energization direction, current integrated value, and the like).

The "terminal voltage" of the oxygen pump cell 14 refers to a voltage between the pair of electrodes 12 and 16 included in the oxygen pump cell 14 or a voltage between one of the pair of electrodes 12 and 16 and a predetermined reference potential. In the embodiment, the terminal voltage of the oxygen pump cell 14 includes an "Ip+ terminal voltage" which is a voltage between the electrode 12 and reference potential or a "Vp voltage" which is a voltage between the electrodes 12 and 16.

Figure 2:
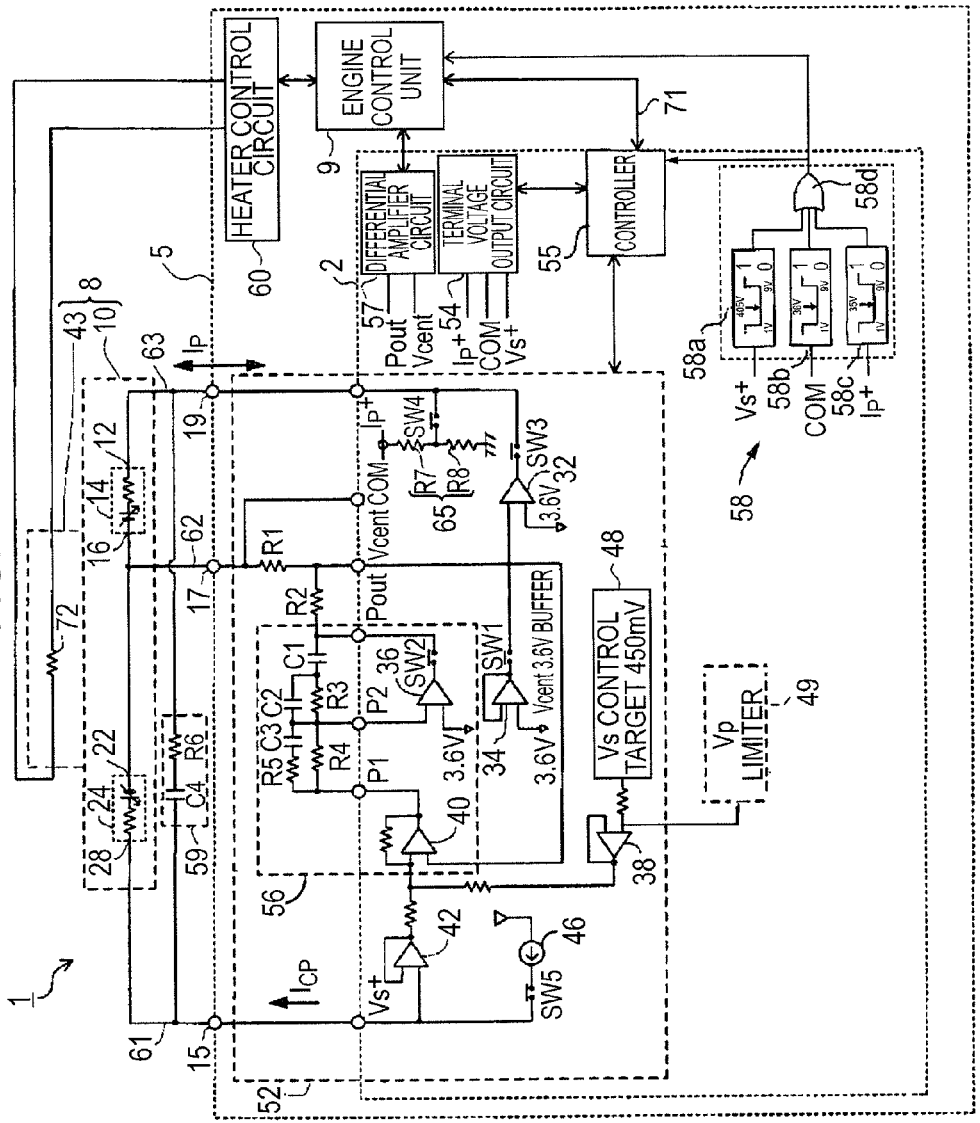
FIG. 2 is a circuit diagram showing an outline configuration of the electronic control unit.

Next, a description will be given, based on FIG. 2, of a configuration and action of the electronic control unit 5. FIG. 2 is a circuit diagram showing an outline configuration of the electronic control unit 5. The electronic control unit 5 includes the sensor control circuit 2, heater control circuit 60, and engine control unit 9, as heretofore described.

The sensor control circuit 2 includes the sensor drive circuit 52, a terminal voltage output circuit 54, the controller 55, a differential amplifier circuit 57, and an anomaly detection circuit 58.

The sensor drive circuit 52 includes an operational amplifier 32 for causing the Ip current which drives the oxygen pump cell 14 to flow, a PID control circuit 56 for improving the control characteristics of the Ip current, a constant current source 46 for causing the constant current Icp to flow through the oxygen concentration sensing cell 24 in such a way as to maintain the oxygen concentration around the second sensing electrode 28 constant, and a constant voltage source 48 which supplies a control target voltage of the Ip current.

Also, the sensor drive circuit 52 includes the connection terminals (the Vs+ terminal, COM terminal, and Ip+ terminal) connecting with the sensor element 10, terminals (a P1 terminal, a P2 terminal, and a Pout terminal) for externally mounting an element which determines the characteristics of the PID control circuit 56, and switches SW1 to SW5 for changing an energization state (an operation mode) of the sensor drive circuit 52 in accordance with the energization state switching command output from the engine control unit 9. The operation mode of the sensor drive circuit 52 represents an energization state in which the sensor element 10 is energized.

Furthermore, the sensor drive circuit 52 includes a Vcent point connected to the COM terminal 17, and an output terminal, to be described hereafter, of the PID control circuit 56, an inverting input terminal of the operational amplifier 32, and an output terminal of an operational amplifier 34 are connected to the Vcent point. The output terminal of the operational amplifier 34 is connected to the Vcent terminal via the switch SW1. Also, an inverting input terminal of the operational amplifier 34 is connected to the output terminal, and a reference voltage 3.6 V is applied to a non-inverting input terminal of the operational amplifier 34. That is, the operational amplifier 34 is a circuit which, as well as applying the reference voltage 3.6 V to the Vcent terminal, supplies an anomaly diagnosis current which carries out an anomaly diagnosis of the sensor element 10, or the like.

The second pump electrode 16 is connected to the Vcent point via the wire 62, the second connection terminal 17, and a resistive element R1.

A voltage dividing circuit 65 and an output terminal of the operational amplifier 32 are connected to the Ip+ terminal. The voltage dividing circuit 65 includes two resistive elements R7 and R8 which divide a constant supply voltage, and a connection point of the resistive elements R7 and R8 is connected to the Ip+ terminal via the switch SW4. Also, the output terminal of the operational amplifier 32 is connected to the Ip+ terminal via the switch SW3. One end of the resistive element R8 is grounded.

The PID control circuit 56 is connected to the inverting input terminal of the operational amplifier 32 via the Vcent terminal and a resistive element R2, and the reference voltage 3.6 V is applied to a non-inverting input terminal of the operational amplifier 32. That is, the operational amplifier 32 configures one portion of a negative feedback circuit which controls a current with which the sensor element 10 (specifically, the oxygen concentration sensing cell 24) is energized.

The PID control circuit 56 has a function of PID computing a deviation amount AVs between 450 mV, which is a control target voltage of the oxygen concentration sensing cell 24, and an output voltage Vs of the oxygen concentration sensing cell 24, and improving the control characteristics of the heretofore described negative feedback circuit. The PID control circuit 56 includes operational amplifiers 36 and 40, resistors R3 to R5, and capacitors C1 to C3.

An output terminal of an operational amplifier 42 is connected to an input terminal of the PID control circuit 56 (an inverting input terminal of the operational amplifier 40), and a non-inverting input terminal of the operational amplifier 42 is connected to the Vs+ terminal. That is, the output voltage Vs of the oxygen concentration sensing cell 24 is input into the PID control circuit 56 via the operational amplifier 42. An inverting input terminal of the operational amplifier 42 is connected to the output terminal.

Also, the constant current source 46 is connected to the Vs+ terminal via the switch SW5. The constant current source 46 is a circuit which supplies the constant current Icp (for example, 17 μA) caused to flow through the oxygen concentration sensing cell 24 in order to maintain the oxygen concentration (in the reference oxygen chamber 26) around the second sensing electrode 28 of the oxygen concentration sensing cell 24 constant.

Also, an output terminal of an operational amplifier 38 is connected to the inverting input terminal of the operational amplifier 40 via a resistive element. The constant voltage source 48 is connected to a non-inverting input terminal of the operational amplifier 38, and an inverting input terminal of the operational amplifier 38 is connected to the output terminal. That is, an output from the constant voltage source 48 is input into the inverting input terminal of the operational amplifier 40 via the operational amplifier 38, and 450 mV, which is the control target voltage which controls the Ip current, is supplied to the PID control circuit 56 via the operational amplifier 40.

An output terminal of the operational amplifier 40 is connected to the P1 terminal, and a non-inverting input terminal of the operational amplifier 40 is connected to the Vcent terminal. Also, a resistive element is interposed between the output terminal and inverting input terminal of the operational amplifier 40. The resistor R5 side of a first series circuit of the resistor R5, capacitor C3, and capacitor C2, and the R4 side of a second series circuit of the resistors R4 and R3, are connected in parallel to the P1 terminal. Also, a connection point of the capacitor C3 and capacitor C2 of the first series circuit is connected to the P2 terminal. In the same way, a connection point of the resistors R4 and R3 of the second series circuit is also connected to the P2 terminal. Furthermore, the capacitor C2 and resistor R3 are connected to the capacitor C1, and the capacitor C1 is connected to the Pout terminal.

In a heretofore known gas sensor, a Vp limiter 49 is connected between the constant voltage source 48 and operational amplifier 38. When the voltage (Vp voltage) between the pair of electrodes 12 and 16 of the oxygen pump cell 14 exceeds a predetermined threshold value at which an overvoltage occurs in the oxygen pump cell 14, the Vp limiter 49 causes the output (control target voltage) from the constant voltage source 48 to shift, thus preventing the overvoltage from being applied to the oxygen pump cell 14.

Herein, the "overvoltage" of the oxygen pump cell 14 refers to a voltage at which an excessive current flows through the oxygen pump cell 14, and a blackening (a phenomenon wherein the cell is blackened due to a loss of oxygen ions) occurs, leading to damage to the cell.

Figure 3:
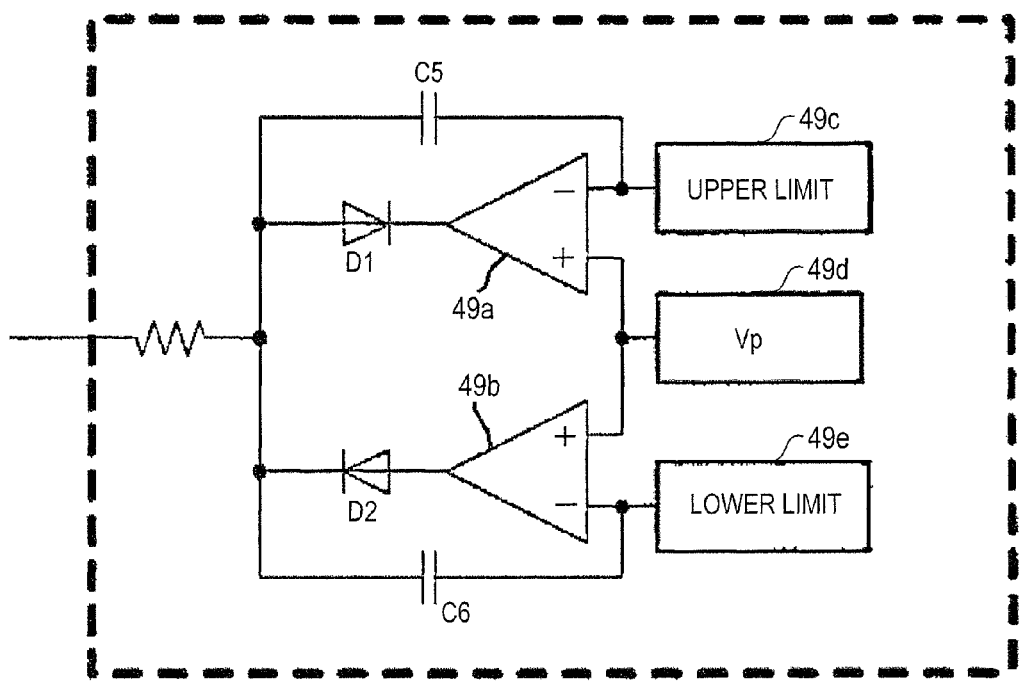
FIG. 3 is a diagram showing a configuration of a common Vp limiter.

FIG. 3 shows a configuration of the common Vp limiter 49. The Vp limiter 49 includes two operational amplifiers 49a and 49b, two diodes D1 and D2, and capacitors C5 and C6. Non-inverting input terminals of the operational amplifiers 49a and 49b are connected to each other. Also, inverting input terminals of the operational amplifiers 49a and 49b are connected to respective output terminals thereof via the capacitors C5 and C6 and via the diodes D1 and D2 respectively, and the Vp limiter 49 carries out a feedback control.

The diode D1 causes only a current from the exterior to the output terminal of the operational amplifier 49a to flow. Meanwhile, the diode D1 causes only a current from the output terminal of the operational amplifier 49a to the exterior to flow.

A predetermined potential (Vp) 49d is applied to the non-inverting input terminal of each of the operational amplifiers 49a and 49b, a predetermined potential (upper limit) 49c is applied to the inverting input terminal of the operational amplifier 49a, and a predetermined potential (lower limit) 49e is applied to the inverting input terminal of the operational amplifier 49b.

Then, when the Vp voltage exceeds the upper limit 49c, a current flows from the exterior to the output terminal of the operational amplifier 49a via the diode D1, lowering the Vs control target voltage of the constant voltage source 48. Meanwhile, when the Vp voltage exceeds the lower limit 49e, a current flows from the output terminal of the operational amplifier 49a to the exterior via the diode D2, raising the Vs control target voltage of the constant voltage source 48.

In the invention, the Vp limiter 49 does not have to be provided, in which case, as well as the sensor drive circuit 52 becoming compact, the number of parts does not increase, and cost is reduced.

Then, the P2 terminal is connected to an inverting input terminal of the operational amplifier 36, and the output terminal of the PID control circuit 56 (an output terminal of the operational amplifier 36) is connected to the Pout terminal via the switch SW2. Meanwhile, the reference voltage 3.6 V is applied to a non-inverting input terminal of the operational amplifier 36.

The Pout terminal is connected to the Vcent terminal via the resistive element R2, and the output terminal (capacitor C1) of the PID control circuit 56 is connected to the COM terminal via the resistive element R2 and resistive element R1.

The resistors R3 to R5 and capacitors C1 to C3, being mounted at the P1 terminal and P2 terminal, are included in order to determine the control characteristics of the PID control circuit 56.

Also, an oscillation prevention circuit 59 formed of a series circuit of the resistor R6 and capacitor C4 is inserted between the Vs+ terminal and Ip+ terminal in order to prevent an oscillation of the sensor drive circuit 52.

Next, a description will be given of other circuits 54, 57, and 58 included in the sensor control circuit 2.

The terminal voltage output circuit 54 outputs terminal voltages of the Vs+ terminal, COM terminal, and Ip+ terminal to the engine control unit 9 via the controller 55. Although connection lines are omitted from the drawing, input terminals of the terminal voltage output circuit 54 are connected to the Vs+ terminal, COM terminal, and Ip+ terminal respectively.

The terminal voltage output circuit 54 corresponds to "terminal voltage output means" in the claims.

The differential amplifier circuit 57 outputs a voltage across the resistive element R2 (specifically, a voltage across the Vcent point and Pout point) to the input port of the engine control unit 9 as the gas detection signal. This voltage is such that the Ip current flowing through the oxygen pump cell 14 is voltage converted by the resistive element R2. The gas detection signal may be output to the input port of the engine control unit 9 via the transmission cable 71.

Next, the anomaly detection circuit 58 is configured of wind comparators 58a, 58b, and 58c and an OR circuit 58d, and an output terminal of each comparator 58a, 58b, and 58c is connected in parallel to an input terminal of the OR circuit 58d. Then, although connection lines are omitted from the drawing, input terminals of the individual comparators are connected to the Vs+ terminal, COM terminal, and Ip+ terminal respectively.

Each wind comparator 58a, 58b, and 58c is configured in such a way as to output a low level signal when the terminal voltage of each of the Vs+ terminal, COM terminal, and Ip+ terminal is within a predetermined voltage range, and output a high level signal when each terminal voltage is out of the predetermined voltage range.

The terminal voltage of the Vs+ terminal is normally maintained at 4.05 V, which is a value wherein the output voltage Vs (450 mV) of the oxygen concentration sensing cell 24 is added to the reference voltage 3.6 V of the COM terminal. However, when the wire 61 or the like (also called a Vs+ line) connected to the Vs+ terminal is short-circuited to a supply potential or ground potential for some reason, the terminal voltage of the Vs+ terminal reaches the supply potential or ground potential. Then, an excessively high anomalous current flows through the sensor element 10, and there is fear that the sensor element 10 is damaged. Therefore, the wind comparator 58a is configured in such a way as to compare the terminal voltage of the Vs+ terminal and a preset threshold value, and output the high level signal when the terminal voltage of the Vs+ terminal exceeds the threshold value.

Specifically, the upper limit of the threshold value of the wind comparator 58a is set at 9 V, or allowing for a fluctuation in the supply voltage of the sensor element control circuit 50, is set at a predetermined voltage value wherein a predetermined value (for example, 1.5 V) is subtracted from the supply voltage, and the lower limit of the threshold value is set at 1 V wherein a ground level of 0 V is allowed for a floating ground. Then, the wind comparator 58a is configured in such a way as to output the high level signal when the terminal voltage of the Vs+ terminal rises above the upper limit 9 V or predetermined voltage value, or when the terminal voltage of the Vs+ terminal drops below the lower limit 1 V.

The terminal voltage of the COM terminal is normally controlled by the operational amplifier 32 so as to become the reference voltage 3.6 V. However, when the wire 62 or the like (also called a COM line) connected to the COM terminal is short-circuited to the supply potential or ground level for some reason, the terminal voltage of the COM terminal reaches the supply potential or ground potential in the same way as that of the Vs+ terminal. Therefore, the wind comparator 58b is configured in such a way as to compare the terminal voltage of the COM terminal and a preset threshold value, and output the high level signal when the terminal voltage of the COM terminal exceeds the threshold value. Specifically, in the same way as with the wind comparator 58a, the upper limit of the threshold value of the wind comparator 58b is set at 9 V or the predetermined voltage value, and the lower limit of the threshold value is set at 1 V. Then, the wind comparator 58b is configured in such a way as to output the high level signal when the terminal voltage of the COM terminal rises above the upper limit 9 V or when the potential of the COM terminal drops below the lower limit 1 V.

At the Ip+ terminal too, when the wire 63 or the like (also called an Ip+ line) connected to the Ip+ terminal is short-circuited to the supply voltage or ground level for some reason, the terminal voltage of the Ip+ terminal reaches the supply potential or ground potential. Therefore, the wind comparator 58c is configured in such a way as to compare the terminal voltage of the Ip+ terminal and a preset threshold value, and output the high level signal when the terminal voltage of the Ip+ terminal exceeds the threshold value. Specifically, with the wind comparator 58c, into which is input the terminal voltage of the Ip+ terminal, too, in the same way as with the wind comparator 58b, the upper limit of the threshold value is set at 9 V or the predetermined voltage value, and the lower limit of the threshold value is set at 1 V, in such a way as to sandwich the reference voltage 3.6 V. Then, the wind comparator 58c is configured in such a way as to output the high level signal when the terminal voltage of the Ip+ terminal rises above the upper limit 9 V or predetermined voltage value, or when the terminal voltage of the Ip+ terminal drops below the lower limit 1 V.

Herein, the heretofore described upper limit is a threshold value at which the Ip+ terminal side wire is short-circuited with a power supply (a battery) which drives the gas sensor, causing a VB short circuit, and the voltage rising to the supply voltage is detected. This upper limit is called a "first threshold value ($V_{BAT}$)" as appropriate. The $V_{BAT}$ is a value of the supply voltage or a value wherein a predetermined value (for example, 1.5 V) is subtracted from the supply voltage, allowing for a fluctuation in the supply voltage.

Meanwhile, the heretofore described lower limit is a threshold value at which the Ip+ terminal side wire is short-circuited with the ground, causing a GND short circuit, and it is determined that the voltage reaches 0. This lower limit is called a "ground threshold value ($V_{GND}$)" as appropriate. The $V_{GND}$ is a value which is made greater than that of the ground potential by a predetermined value (for example, 1 V) allowing for a fluctuation in the supply voltage.

Then, when the Ip+ terminal voltage exceeds the $V_{BAT}$ or becomes less than the $V_{GND}$, an anomaly is detected by the OR circuit 58d below.

The OR circuit 58d calculates a logical sum of signals from the individual wind comparators 58a, 58b, and 58c, and when the high level signal is input from one of the wind comparators 58a, 58b, and 58c, sets an anomaly detection flag DIAG to DIAG=1, and outputs it to the engine control unit 9 and controller 55. When the terminal voltage of each of the Vs+ terminal, COM terminal, and Ip+ terminal is within the predetermined voltage range, the anomaly detection circuit 58 sets the anomaly detection flag DIAG to DIAG=0, and outputs it to the engine control unit 9 and controller 55. In this way, the anomaly detection circuit 58 has a function of setting the anomaly detection flag DIAG to DIAG=1 when a short circuit anomaly occurs in one of the Vs+ line, COM line, and Ip+ line, and the terminal voltages of the Vs+ terminal, COM terminal, and Ip+ terminal exceed the first threshold value ($V_{BAT}$) and reach an anomalous voltage value (in other words, when an anomaly occurs in the sensor element 10).

The anomaly detection circuit 58 corresponds to "anomaly detection means" in the claims.

The sensor drive circuit 52 configured in the way heretofore described, based on the command from the engine control unit 9, switches between a turning on and turning off of each switch SW1 to SW5, and sets the energization state (operation mode) of the sensor drive circuit 52 itself to one of a gas concentration measuring energization state (hereafter an "A mode" as appropriate), a sensor protection energization state (hereafter a "P mode" as appropriate), and a pre-activation energization state (hereafter an "NA mode" as appropriate). Each energization state will be described hereafter.

The engine control unit 9 outputs from the output port the command to switch the energization state of the sensor drive circuit 52 (specifically, a control signal which carries out an on/off control of each switch SW1 to SW5), and outputs the command to the sensor control circuit 2 (the controller 55 thereof) via the transmission cable 71. Then, the controller 55 switches (sets) the energization state of the sensor drive circuit 52.

Also, the gas detection signal indicating the voltage across the resistive element R2 is input directly into the input port of the engine control unit 9 via the differential amplifier circuit 57. Furthermore, the anomaly detection flag DIAG from the anomaly detection circuit 58, as well as being input directly into the input port of the engine control unit 9, is also input into the controller 55. Meanwhile, an output signal from the terminal voltage output circuit 54 is input into the controller 55, and input into the input port of the engine control unit 9 via the transmission cable 71. An element resistance value signal indicating the electric resistance value and temperature of the sensor element 10 is also input into the controller 55, and input into the input port of the engine control unit 9 via the transmission cable 71.

In this way, the engine control unit 9, as well as being able to control the energization state of the sensor drive circuit 52, can detect the presence or absence of an anomaly of the sensor element 10 based on the input signals from the anomaly detection circuit 58 and terminal voltage output circuit 54. Specifically, the engine control unit 9, by identifying to which one of identification conditions the condition of each input terminal voltage applies, can detect a terminal at which an anomaly has occurred and the contents of the anomaly (a power supply short circuit (the VB short circuit), a ground short circuit (a ground short circuit), or the like).

Also, when the Ip+ terminal voltage exceeds the first threshold value ($V_{BAT}$), the anomaly detection circuit 58 outputs an anomaly signal to the controller 55 too, meaning that the controller 55 can also switch the energization state of the sensor drive circuit 52 itself directly to the P mode without depending on the determination of the engine control unit 9.

Next, referring to FIG. 4, a description will be given of the energization state (operation mode) of the sensor drive circuit 52 when switching between the turning on and turning off of each switch SW1 to SW5.

Herein, the sensor protection energization state is a condition in which the gas sensor 8 is protected by cutting off the electrical connection of the sensor element 10 and sensor drive circuit 52 so as to prevent a current from flowing through the gas sensor 8.

Also, the gas concentration measuring energization state is a condition in which the value and direction of a current flowing through the oxygen pump cell 14 are controlled in such a way that the voltage between both electrodes of the oxygen concentration sensing cell 24 reaches a desired value, thus enabling a gas concentration measurement.

The pre-activation energization state is a condition in which both electrodes of at least one of the oxygen concentration sensing cell 24 and oxygen pump cell 14 are energized with a minute current in order that no overvoltage is applied to the gas sensor 8 (the two cells 14 and 24 thereof). As a more specific pre-activation energization state, in the case of a gas sensor of a configuration wherein the electrode 28, of the pair of electrodes provided on the oxygen concentration sensing cell 24, on a side not facing the measuring chamber is closed to the exterior, it is possible to cite an energization state in which a minute current is caused to flow through the oxygen concentration sensing cell 24 in order to cause the electrode 28 to work as an internal oxygen reference source.

Firstly, in the gas concentration measuring energization state, the switches SW2, SW3, and SW5 of the sensor drive circuit 52 are turned on, and the switches SW1 and SW4 are turned off. The gas concentration measuring energization state is an operation mode in which a state in which it is possible to energize the gas sensor 8 (specifically, the oxygen pump cell 14) with a comparatively high current is set for a pumping of oxygen or the like. At this time, a maximum current value with which the oxygen pump cell 14 can be energized is fixed by the current drivability of the operational amplifier 32 and operational amplifier 36, and in the embodiment, is set to the order of 20 [mA].

Then, for example, when the measured gas falls into a fuel oversupply (rich), the measuring chamber 20 has a deficiency of oxygen concentration below the theoretical air-fuel ratio, and the output voltage Vs of the oxygen concentration sensing cell 24 becomes higher than 450 mV, which is the control target voltage. Consequently, the deviation amount ΔVs between the control target voltage and output voltage Vs occurs, the deviation amount ΔVs is PID computed by the PID control circuit 56, and fed back by the operational amplifier 32. Because of this, the Ip current for pumping a deficiency of oxygen into the measuring chamber 20 with the oxygen pump cell 14 flows through the oxygen pump cell 14.

Meanwhile, when the measured gas falls into a fuel undersupply (lean), the measuring chamber 20 has an excess of oxygen concentration over the theoretical air-fuel ratio, and the output voltage Vs of the oxygen concentration sensing cell 24 becomes lower than the control target voltage 450 mV, meaning that the deviation amount ΔVs is fed back by the operational amplifier 32 in the same way as heretofore described, and the Ip current for pumping an excess of oxygen from the measuring chamber 20 with the oxygen pump cell 14 flows through the oxygen pump cell 14.

By so doing, it is possible to compute the oxygen concentration in the measured gas based on the Ip current energization state (the energization direction, current integrated value, and the like).

Next, in the sensor protection energization state, all the switches SW1 to SW5 of the sensor drive circuit 52 are turned off. Because of this, signals input into the sensor element 10 from the operational amplifiers 32, 34, and 36 and constant current source 46 are turned off, and energization from the sensor drive circuit 52 to the sensor element 10 is cut off.

Consequently, when a wire anomaly occurs, and the anomaly detection flag DIAG (=1) is output from the OR circuit 58*d*, the engine control unit 9 outputs the switching command to the controller 55, and by the controller 55, based on this command, setting the sensor drive circuit 52 to the sensor protection energization state, it is possible to prevent an anomalous current from continuously flowing through the sensor element 10, and it is possible to protect the sensor element 10.

In the pre-activation energization state, the switches SW1, SW4, and SW5 of the sensor drive circuit 52 are turned on, and the switches SW2 and SW3 are turned off. At this time, as the switch SW3 is off, no more current is supplied from the operational amplifier 32 driving the oxygen pump cell 14, and also, as the switch SW2 is off, no more current is supplied from the operational amplifier 36 either, meaning that a current control over the oxygen pump cell 14 is stopped. Consequently, in the pre-activation energization state, the negative feedback control of the oxygen pump cell 14 is no longer carried out.

Also, as the switches SW1, SW4, and SW5 are on, the minute constant current Icp is supplied to the oxygen pump cell 14 and oxygen concentration sensing cell 24 from the operational amplifier 34, constant current source 46, and voltage dividing circuit 65. Because of this, oxygen is pumped from the first sensing electrode 22 to the second sensing electrode 28 side, and oxygen of an approximately constant concentration is accumulated in the reference oxygen chamber 26 formed around the second sensing electrode 28.

In this way, in the pre-activation energization state, as only the minute current is supplied to the sensor element 10, it does not happen that an excessively high current is supplied even when a wire anomaly occurs, meaning that it becomes difficult for damage (a blackening or the like) to the sensor element 10 to occur.

Also, the engine control unit 9 detects a wire anomaly based on the condition of each input terminal voltage, as heretofore described, but as each terminal voltage is low in the pre-activation energization state, it is possible to carry out the detection of a wire anomaly without the sensor element 10 being damaged.

For example, in a wire anomaly condition in which the wire 62 is short-circuited with the ground (ground shorted), when the gas concentration measuring energization state is set, an energizing path is formed from the operational amplifier 32 via the oxygen pump cell 14 and wire 62 to the ground line, and the maximum current of the current drivability of the operational amplifier 32 is supplied from the operational amplifier 32 to the oxygen pump cell 14. In this case, a condition occurs in which the oxygen pump cell 14 is energized with an excessively high current, leading to damage (a blackening or the like) to the sensor element 10 instantaneously. As opposed to this, when the wire 62 is short-circuited with the ground, although an energizing path is formed from the voltage dividing circuit 65 via the oxygen pump cell 14 and wire 62 to the ground line in the case of the pre-activation energization state, a current supplied from the voltage dividing circuit 65 to the oxygen pump cell 14 is minute. Because of this, it does not happen that the oxygen pump cell 14 is energized with an excessively high current, and it is possible to prevent the sensor element 10 from being damaged (blackened or the like).

Next, a description will be given of details of the oxygen pump cell protection process which, being a portion of the feature of the invention, is executed by the engine control unit 9.

In the invention, in order that it is possible to prevent an overvoltage from being applied to the oxygen pump cell, a configuration is such as to generate a cell voltage anomaly signal (for example, a cell voltage anomaly flag) and switch to the P mode when the Ip+ terminal voltage of the oxygen pump cell 14 becomes equal to or higher than the above-mentioned overvoltage (or a predetermined voltage value wherein a predetermined value (for example, 8 V) is subtracted from the above-mentioned overvoltage, allowing for a fluctuation in the supply voltage of the sensor control circuit 2).

Herein, the above-mentioned overvoltage or the above-mentioned predetermined voltage value corresponds to a "second threshold value" in the claims. The second threshold value is a voltage at which the overvoltage is (assumed to be) applied to the oxygen pump cell.

As heretofore described, a configuration is originally such that the anomaly detection circuit 58 detects an anomaly when the Ip+ terminal voltage exceeds the first threshold value ($V_{BAT}$) or becomes less than the $V_{GND}$, along with which the engine control unit 9 causes the gas sensor 8 to shift to the P mode (in which the sensor drive circuit 52 is in a de-energized condition). Consequently, as an anomaly is detected on the anomaly detection circuit 58 side when the Ip+ terminal voltage rises above the $V_{BAT}$, in the following oxygen pump cell protection process, the engine control unit 9 carries out the process in accordance with a result of the detection of the anomaly detection circuit 58, and does not detect the anomaly itself. Herein, when the Ip+ terminal voltage exceeds the first threshold value, the anomaly detection circuit 58 outputs a short circuit anomaly signal (for example, a short circuit anomaly flag).

Then, in the oxygen pump cell protection process, it is sufficient to generate the cell voltage anomaly signal when the Ip+ terminal voltage is less than the first threshold value ($V_{BAT}$) and equal to or more than the second threshold value.

Also, in the invention, a configuration may be such as to switch to the P mode when the above-mentioned cell voltage anomaly signal continues even after the elapse of a "second predetermined time". Normally, when a transition is made from the NA mode to the A mode, the Ip current is caused to flow in a condition in which the resistance of the oxygen pump cell 14 is high, meaning that the Ip+ terminal voltage increases above the second threshold value temporarily. In this kind of case too, the heretofore described cell voltage anomaly signal is generated. However, in the event that the gas sensor is normal, the Ip+ terminal voltage drops to less than the second threshold value in the order of several seconds.

Therefore, it is possible to prevent a false detection of an anomaly by setting the "second predetermined time" as the above-mentioned predetermined time, allowing for a time for which the Ip+ terminal voltage which has once risen drops, and determining that the voltage of the oxygen pump cell 14 is actually anomalous when the cell voltage anomaly signal is generated even after the elapse of the second predetermined time.

Figure 5:
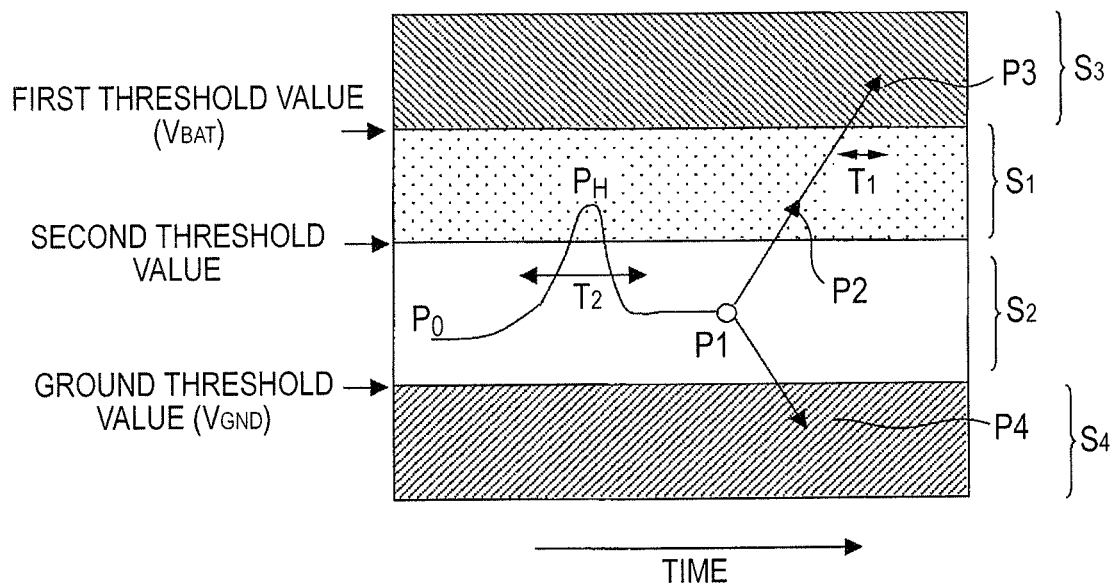
FIG. 5 is a diagram showing a temporal change in an Ip+ voltage of an oxygen pump cell after activating a gas sensor.

FIG. 5 schematically shows a temporal change in the Ip+ terminal voltage of the oxygen pump cell 14 after the gas sensor 8 is activated. In FIG. 5, when the gas sensor is activated ($P_O$), a transition is made from the NA mode to the A mode, as heretofore described, and the Ip current flows in the condition in which the resistance of the oxygen pump cell 14 is high. For this reason, the Ip+ terminal voltage increases above the second threshold value temporarily ($P_H$). At this time, by setting the heretofore described second predetermined time $T_2$ to be longer than a time for which the Ip+ terminal voltage which has risen at $P_H$ drops, it does not happen that the rise in the Ip+ terminal voltage caused by the transition from the NA mode to the A mode is falsely detected as an anomaly.

Then, when the oxygen pump cell 14 stabilizes, a gas concentration measurement in the A mode is carried out in a stable region $S_2$ between the second threshold value and $V_{GND}$. However, when an anomaly occurs in the oxygen pump cell 14 at $P_1$, and the voltage rises to a region $S_1$ less than the first threshold value ($V_{BAT}$) and equal to or more than the second threshold value, the cell voltage anomaly signal is generated by the heretofore described oxygen pump cell protection process, and the gas sensor 8 is switched to the P mode and protected.

When the Ip+ terminal voltage rises to a region $S_3$ exceeding the first threshold value ($V_{BAT}$) ($P_3$), or when the Ip+ terminal voltage drops to a region $S4$ less than the $V_{GND}$ ($P_4$), the anomaly detection circuit 58 included in a heretofore known gas sensor control apparatus detects an anomaly, and switches the gas sensor 8 to the P mode.

At this time, as there is a possibility that the cell is short-circuited when the Ip+ terminal voltage rises above the first threshold value, it is necessary to immediately switch the gas sensor 8 to the P mode and protect it. Therefore, when the Ip+ terminal voltage rises above the first threshold value, it is sufficient to determine that there is great urgency, and carry out a process (output a de-energization command) in such a way as to switch to the P mode immediately after the first predetermined time T1 shorter than the second predetermined time has elapsed. As opposed to this, when the cell voltage anomaly signal with less urgency is received, it is sufficient to output the de-energization command when the second predetermined time later than the first predetermined time elapses.

In the embodiment, with the engine control unit 9, a sensor energization control process which is a main routine is carried out, and the heretofore described oxygen pump cell protection process is invoked as a sub-routine and executed. Consequently, firstly, a description will be given of the sensor energization control process which is the main routine.

Firstly, the engine control unit 9 (and the controller 55 of the sensor control circuit 2), as well as being activated by the internal combustion control system 1 being powered on, executes an initialization process (an initialization of an internal variable or the like, or the like), and after completing the initialization process, starts the following various kinds of control process.

As the various kinds of control process, there are a specified gas concentration detection process which detects a specified gas concentration in the exhaust gas based on the gas detection signal from the sensor control circuit 2, or the like, the command output process which outputs the energization state switching command to the sensor control circuit 2, an air-fuel ratio control process for carrying out an air-fuel ratio control of the engine using the specified gas concentration (oxygen concentration) detected based on the gas detection signal, and the like.

Then, the engine control unit 9 starts the initialization process by an automobile being powered on, and after completing the process, executes the sensor energization control process for controlling the energization state in which the sensor element 10 is energized as one of the various kinds of control process. In the sensor energization control process, the engine control unit 9, based on various conditions, determines an optimum energization state as the energization state in which the sensor element 10 is energized, and executes a process which outputs the switching command in accordance with an energization state which is a result of the determination to the sensor control circuit 2.

As a method of determining the optimum energization state, for example, the pre-activation energization state is determined to be the optimum energization state under conditions such as immediately after the sensor activation, and the gas concentration measuring energization state is determined to be the optimum energization state under conditions whereby the sensor element 10 comes into an activated condition.

As the engine control unit 9 has received a present state flag representing a present energization state from the sensor control circuit 2, it is possible to know the present energization state based on the present condition flag.

As a more specific method of determining the optimum energization state, it is determined based on the element resistance value signal from the gas sensor whether or not the gas sensor is activated, and the pre-activation energization state is determined to be the optimum energization state when the gas sensor is not activated, while the gas concentration measuring energization state is determined to be the optimum energization state when the gas sensor is activated. Then, when it is determined by the anomaly detection circuit 58 that the gas sensor or energizing path is anomalous, the energization state is switched to the sensor protection energization state (P mode). Also, when it is determined by the anomaly detection circuit 58 that the anomaly of the gas sensor or energizing path has been eliminated, the optimum energization state is determined based on the element resistance value signal from the gas sensor. Furthermore, when the Ip+ terminal voltage of the oxygen pump cell 14 indicates an anomalous value, the oxygen pump cell protection process, to be described hereafter, is carried out, except for a condition that the anomaly detection circuit 58 detects the anomaly.

The element resistance value signal refers to a signal which, a current or voltage of a predetermined size being periodically supplied to one of the oxygen pump cell 14 and oxygen concentration sensing cell 24 which configure the gas sensor 8, can be obtained via the cell at this time. As the element resistance value signal is a signal which can be acquired by a heretofore known technique (circuit configuration), a description in the embodiment is omitted. However, specifically, a configuration is such that a current of a predetermined size is periodically caused to flow through the oxygen concentration sensing cell 24, an output obtained via the oxygen concentration sensing cell 24 at this time is sampled and held, and the sampled and held output is output to the engine control unit 9 as the element resistance value signal.

Figure 6:
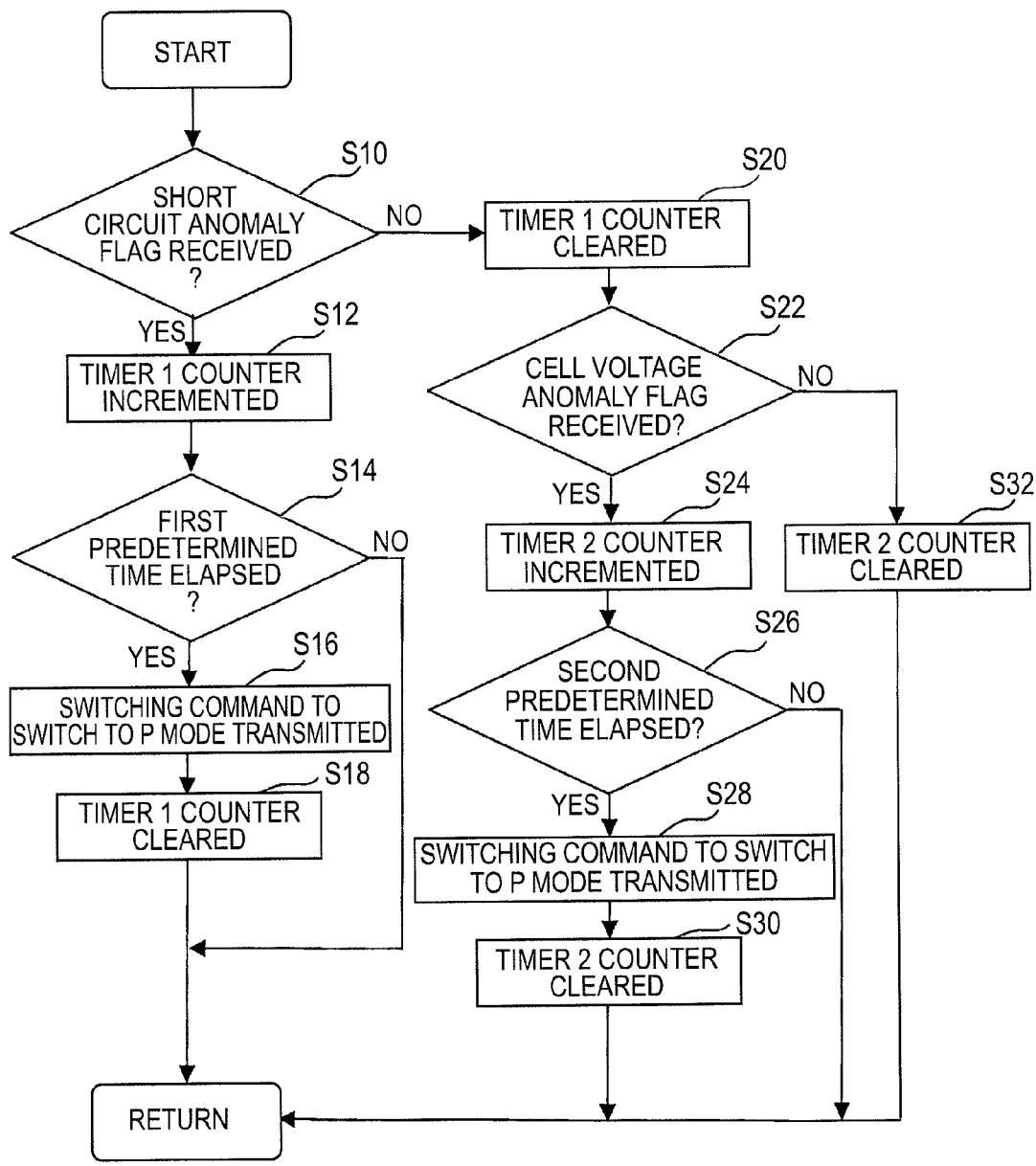
FIG. 6 is a diagram showing a flowchart of an oxygen pump cell protection process.

Next, referring to FIG. 6, a description will be given of the heretofore described oxygen pump cell protection process in the gas sensor control unit according to the embodiment of the invention.

When the oxygen pump cell protection process is activated by the automobile being powered on, firstly, the engine control unit 9 determines whether or not it has received the short circuit anomaly flag from the anomaly detection circuit 58 (step S10).

On receiving the short circuit anomaly flag in step S10, the engine control unit 9 starts (increments) a timer 1 (step S12), and determines whether or not the first predetermined time has elapsed from step S12 (step S14). Then, if the first predetermined time has elapsed, the engine control unit 9 outputs the switching command to switch to the P mode (sensor protection energization state) to the controller 55 (step S16), clears the timer 1 (step S18), and returns to the start of the oxygen pump cell protection process.

Meanwhile, if the first predetermined time has not elapsed from step S12, the engine control unit 9 also returns to the start of the oxygen pump cell protection process.

Meanwhile, the engine control unit 9, if it has not received the short circuit anomaly flag in step S10, clears the timer 1 (step S20), and determines whether or not it has received the cell voltage anomaly flag from the controller 55 (step S22).

Herein, the controller 55 generates the "cell voltage anomaly flag" in the following way. Firstly, the controller 55 receives the terminal voltage of the Ip+ terminal from the terminal voltage output circuit 54. Then, the controller 55 determines whether or not the Ip+ terminal voltage is in the region $S_1$ less than the first threshold value ($V_{BAT}$) and equal to or more than the second threshold, and if the determination result is in the affirmative, generates the cell voltage anomaly flag. This determination process of the controller 55 being carried out at comparatively short time intervals (of the order of one millisecond), shorter than the heretofore described first predetermined time $T_1$ (normally, of the order of three seconds), can rapidly detect an anomaly of the Ip+ terminal voltage.

On receiving the cell voltage anomaly flag in step S22, the engine control unit 9 starts (increments) a timer 2 (step S24), and determines whether or not the second predetermined time has elapsed from step S24 (step S26). If the second predetermined time has elapsed, the engine control unit 9 outputs the switching command to switch to the P mode (sensor protection energization state) to the controller 55 (step S28), clears the timer 2 (step S30), and returns to the start of the oxygen pump cell protection process.

In the case of "Yes" in step S26, the engine control unit 9 receives the cell voltage anomaly flag even after the elapse of the second predetermined time, meaning that there is no false detection or transient phenomenon caused by the transition from the NA mode to the A mode. Consequently, the controller 55 switches the sensor drive circuit 52 to the P mode in accordance with the switching command, and the gas sensor 8 (the oxygen pump cell 14 thereof) is protected.

Meanwhile, if the second predetermined time has not elapsed from step S26, the engine control unit 9 returns to the start of the oxygen pump cell protection process. This means that the Ip+ terminal voltage has dropped to less than the second threshold after the elapse of the second predetermined time, indicating that the anomaly detection in step S26 is false, or that there is a transient phenomenon caused by the transition from the NA mode to the A mode.

As opposed to this, the engine control unit 9, if it has not received the cell voltage anomaly flag in step S22, clears the timer 2 (step S32), and returns to the start of the oxygen pump cell protection process.

In the embodiment, the process of the terminal voltage output circuit 54 outputting the terminal voltage of the Ip+ terminal to the controller 55 and the process of the controller 55 outputting the Ip+ terminal voltage to the engine control unit 9 correspond to a "terminal voltage output step" in the claims.

The process of the controller 55 determining whether or not the Ip+ terminal voltage is less than the first threshold value and equal to or more than the second threshold value, and generating the cell voltage anomaly flag if the determination result is in the affirmative, corresponds to a "cell voltage anomaly signal generation step" in the claims.

The process in the engine control unit 9 in steps S16 and S28, and the process of the controller 55 receiving the switching command transmitted in steps S16 and S28 and the sensor drive circuit 52 being set to the P mode on the controller 55 side, correspond to a "de-energization setting step" in the claims.

Furthermore, the process of the short circuit anomaly signal being output to the engine control unit 9 by the anomaly detection circuit 58 when the Ip+ terminal voltage becomes equal to or more than the first threshold value corresponds to an "anomaly detection step" in the claims.

Apart from the heretofore described embodiment, a configuration may be such that the short circuit anomaly signal generated by the anomaly detection circuit 58 is output to the engine control unit 9 and controller 55, and the controller 55 itself which has received the short circuit anomaly signal switches the sensor drive circuit 52 to the P mode, thus protecting the gas sensor 8 (the oxygen pump cell 14 thereof).

By so doing, it is possible to rapidly switch the sensor drive circuit 52 to the P mode without waiting for the switching command from the engine control unit 9, and it is possible to more quickly prevent an anomalous current from flowing through the sensor element 10.

The invention is not limited to the heretofore described embodiment, and it goes without saying that the invention covers various modifications and equivalents included in the concept and scope of the invention. For example, the linear air-fuel ratio sensor is cited as the sensor element 10, but the invention, not being limited to this, can also be applied to an $NO_X$ sensor including two measuring chambers by adding another cell to the sensor element 10.

However, in the case of the $NO_X$ sensor, as the control of the gas sensor is collectively carried out by one microcomputer (controller), the command means, controller, terminal voltage output means, and sensor drive circuit are all realized in the one controller. Also, the controller corresponds to the gas sensor control apparatus.

DESCRIPTION OF REFERENCE NUMERALS AND SIGNS

1 Gas sensor control apparatus (internal combustion control system)
2 Sensor control circuit
5 Electronic control unit
8 Gas sensor
9 Command means (engine control unit)
13 Solid electrolyte body
14 Oxygen pump cell 12, 16 Pair of electrodes (first pump electrode and second pump electrode)
52 Sensor drive circuit
54 Terminal voltage output means (terminal voltage output circuit)
55 Controller
58 Anomaly detection means (anomaly detection circuit)
$S_1$ Voltage range less than first threshold value and equal to or more than second threshold value
$T_1$ First predetermined time
$T_2$ Second predetermined time

The invention claimed is:

1. A gas sensor control apparatus comprising:
   a gas sensor having at least an oxygen pump cell including a solid electrolyte body and a pair of electrodes provided on the solid electrolyte body;
   a sensor drive circuit which, being connected to the gas sensor, energizes the gas sensor in order to drive the gas sensor;
   terminal voltage output means configured to output a terminal voltage of the oxygen pump cell;
   anomaly detection means configured to compare the terminal voltage and a first threshold value, and when the terminal voltage exceeds the first threshold value, outputs a short circuit anomaly signal informing of a short circuit between a supply voltage which drives the gas sensor and the electrodes, and when the terminal voltage does not exceed the first threshold value, the anomaly detection means compares the terminal voltage and a ground threshold value less than the first threshold value, and when the terminal voltage is less than the ground threshold value, outputs a GND short circuit anomaly signal informing of a short circuit between a ground voltage and the electrode;
   a controller configured to compare the terminal voltage and a second threshold value less than the first threshold value and more than the ground threshold value when the terminal voltage is less than the first threshold value and more than the ground threshold value, and when the terminal voltage exceeds the second threshold value, generate a cell voltage anomaly signal informing of an application of an overvoltage of the oxygen pump cell, but not informing of a short circuit, of the oxygen pump cell; and
   command means programmed to, in response to receiving the short circuit anomaly signal or the cell voltage anomaly signal, output a de-energization command for setting the sensor drive circuit to be de-energized.

2. The gas sensor control apparatus according to claim 1, wherein the command means outputs the de-energization command after the elapse of a first predetermined time from receiving the short circuit anomaly signal, and
   wherein the command means outputs the de-energization command after the elapse of a second predetermined time longer than the first predetermined time from receiving the cell voltage anomaly signal.

3. A control method of a gas sensor control apparatus including:
   a gas sensor having at least an oxygen pump cell including a solid electrolyte body and a pair of electrodes provided on the solid electrolyte body; and
   a sensor drive circuit which, being connected to the gas sensor, energizes the gas sensor in order to drive the gas sensor, the method comprising:
   a terminal voltage output step which outputs a terminal voltage of the oxygen pump cell;
   an anomaly detection step which compares the terminal voltage and a first threshold value, and when the terminal voltage exceeds the first threshold value, outputs a short circuit anomaly signal informing of a short circuit between a supply voltage which drives the gas sensor and the electrodes, and when the terminal voltage does not exceed the first threshold value, the anomaly detection step compares the terminal voltage and a ground threshold value less than the first threshold value, and when the terminal voltage is less than the ground threshold, outputs a GND short circuit anomaly signal informing of a short circuit between a supply voltage and the electrodes;
   a cell voltage anomaly signal generation step which compares the terminal voltage and a second threshold value less than the first threshold value and more than the ground threshold value when the terminal voltage is less than the first threshold value and more than the ground threshold value, and when the terminal voltage exceeds the second threshold value, generates a cell voltage anomaly signal informing of an application of an overvoltage of the oxygen pump cell, but not informing of a short circuit of the oxygen pump cell; and
   a de-energization setting step which, when receiving, by a control unit, the short circuit anomaly signal or the cell voltage anomaly signal, sets, by the control unit, the sensor drive circuit to be de-energized.

4. The gas sensor control method according to claim 3, wherein, in the de-energization setting step, the sensor drive circuit is set to be de-energized after the elapse of a first predetermined time from receiving the short circuit anomaly signal, and
   wherein, in the de-energization setting step, the sensor drive circuit is set to be de-energized after the elapse of a second predetermined time longer than the first predetermined time from receiving the cell voltage anomaly signal.

* * * * *